United States Patent [19]

Bartholomay

[11] 4,389,906
[45] Jun. 28, 1983

[54] AUTOMATIC CROSSCUT SAMPLER

[75] Inventor: Donald O. Bartholomay, Minneapolis, Minn.

[73] Assignee: Gustafson, Inc., Eden Prairie, Minn.

[21] Appl. No.: 117,954

[22] Filed: Feb. 4, 1980

[51] Int. Cl.³ .............................................. G01N 1/20
[52] U.S. Cl. ................................................. 73/863.55
[58] Field of Search ............ 73/863.44, 863.55, 863.56

[56] References Cited

U.S. PATENT DOCUMENTS

| | | | |
|---|---|---|---|
| 3,393,567 | 7/1968 | Jirik | 73/863.55 |
| 3,474,675 | 10/1969 | Strand | 73/863.55 |
| 3,751,991 | 8/1973 | Fisher et al. | 73/863.56 |
| 4,026,155 | 5/1977 | Joseph | 73/863.55 |
| 4,170,900 | 10/1979 | Ozawa | 73/863.56 |
| 4,215,579 | 8/1980 | Hines et al. | 73/863.56 |

*Primary Examiner*—S. Clement Swisher

*Attorney, Agent, or Firm*—Peterson, Palmatier, Sturm, Sjoquist & Baker, Ltd.

[57] ABSTRACT

A sealed housing having entrance and exit ports at its upper and lower surfaces for connection into a vertically extending gravity spout, with a collecting head mounted within the housing for swinging movement across the central flow passage extending from the entrance port to the exit port. The collecting head has an elongate opening confronting the entrance port, such that particulate matter flowing through the housing will be collected within the interior of the collecting head and passed out of the housing through a discharge tube, for sampling. Rotary air cylinders disposed on top of the sealed housing adjacent the entrance port effect swinging movement of the collecting head about an axis parallel to that of the central flow passage, such that the collecting head passes entirely through the particulate flow, from one side of the product stream to the other, thereby assuring a representative sample.

6 Claims, 8 Drawing Figures

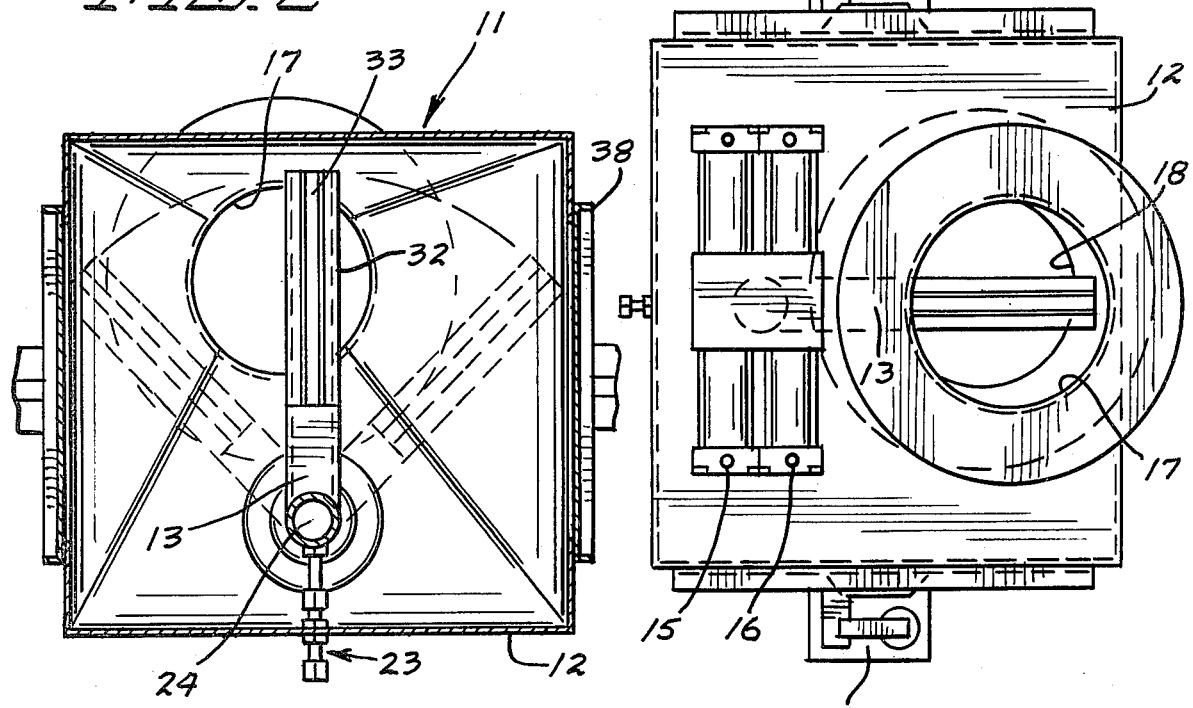
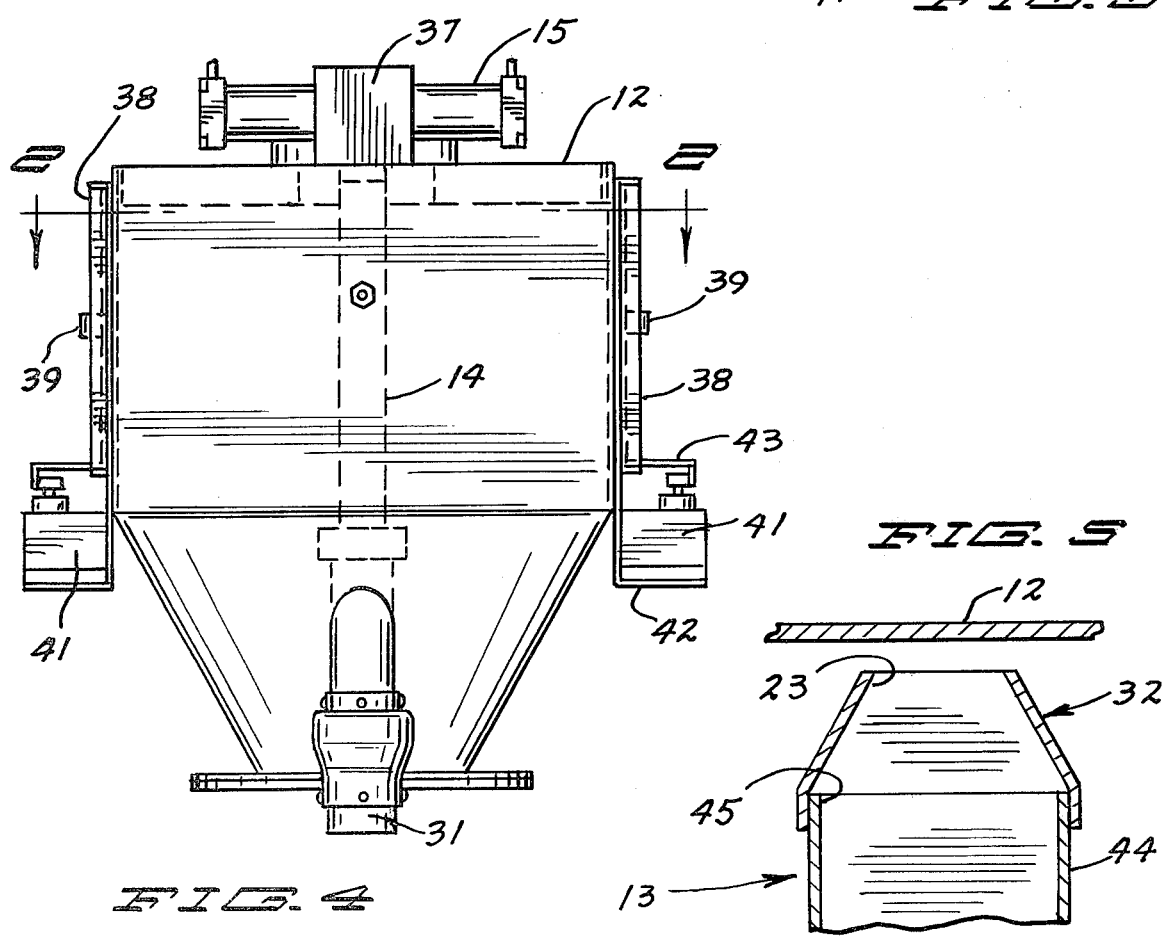

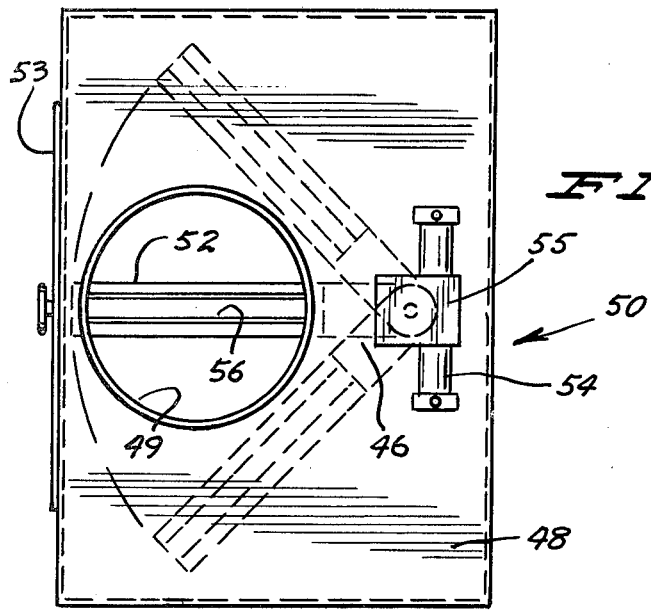
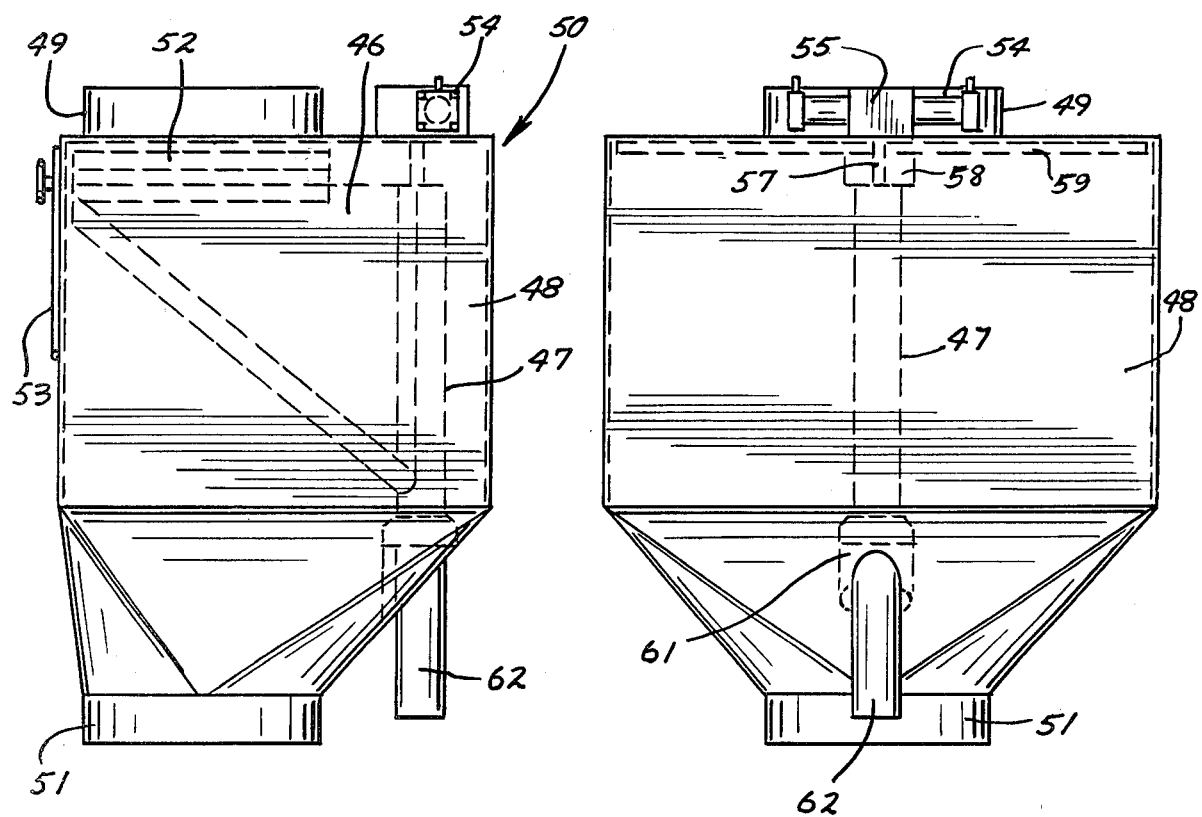

AUTOMATIC CROSSCUT SAMPLER

BACKGROUND OF THE INVENTION

This invention relates to sampling systems, and more particularly to apparatus for drawing representative samples of free-flowing powder, granular, or flake type material as it flows through an angular or vertical gravity spout.

In most conveying or dispensing systems particulate material is not spread uniformly throughout the cross-sectional area of the conveying or dispensing tube, such that there often tends to be a concentration of the particulate material at one side of the tube. Where the particulate material comprises a mixture of two or more substances with different characteristics, the substances may be collected together at one side or another in the tube, rather than being spread uniformly across the tube. As a result, it is not possible to simply insert a probe into the conveying tube and extract a sample, since such procedure will not provide a truly representative sample. Also, dust problems often arise in the systems because of the exceedingly small size of particles conveyed, resulting in further complications for sampling apparatus.

Sampling apparatus, such as that disclosed in Clements, U.S. Pat. No. 4,120,203, is available for connection to the pipe of a pneumatic conveying system for drawing representative samples of the material, as it flows through the conveying pipe. Such constructions typically move a sample collecting head, having an elongated sample receiving slot, across the particulate stream from one side of the stream to the other. In applications for gravity systems extensive rail assemblies must be disposed adjacent the sealed housing containing the sample collecting head, for accommodating movement of the collecting head from one side of the particulate stream to the other within such housing. That is, the overall size of such sampling apparatus has been determined primarily by the mechanism for moving the collecting head through its collecting cycle. In addition to taking up too much space, conventional sampler apparatus also can be vulnerable to dust problems, because of the greater number of components utilized. There is presently available no sampler apparatus capable of withdrawing a representative sample from a conveying or dispensing system while occupying a minimum of space in such system.

SUMMARY OF THE INVENTION

In accordance with this invention there is provided an improved automatic crosscut sampler connected across the spout of a conveying or dispensing system and accommodating substantially free and unobstructed flow of particulate matter through the system. The sampler can be used in angular or vertical gravity systems at atmospheric, positive or negative pressure.

In its non-collecting position, the sample collecting head of the sampler will be disposed to the side of the particulate stream flowing through the spout. The collecting head is swingable about an axis parallel to the particulate stream such that the head can be swung in one direction entirely across the stream; and the collecting head has an elongate sample receiving slot confronting the entrance port of the sampler and extending entirely across the stream. The collecting head may pass only once across the stream in each sampling cycle, or it may move across the stream and then back again to its original position in a single sampling cycle.

It is a primary object of this invention to provide a crosscut sampler capable of collecting representative samples of particulate matter during a spouting operation while occupying as little space as possible.

It is another object of this invention to provide a compact, dust tight sampler that can be used in angular or vertical gravity systems at atmospheric, positive or negative pressure.

It is a further object of this invention to provide a trouble-free crosscut sampler having a minimum of moving parts, and being inexpensively manufactured and maintained.

The collecting head is mounted within the sealed housing of the sampler such that it can be swung across the particulate stream, from one side to the other. The sealed housing need be only large enough to accommodate the movable head, and, accordingly, can be only slightly larger in size than the spout of the conveying or dispensing system itself.

The use of a swingable collecting head eliminates the need for more complicated components to move collecting means across the particulate stream. This together with the size reduction of the housing permits more effective sealing of the sampler, to avoid any problems with dust.

Accordingly, the sampler of this invention is significantly smaller in size than conventional samplers, and yet allows trouble free collection of representative samples of particulate matter. It can be inexpensively manufactured and maintained, with complete avoidance of dust problems. The collecting head can be swung across the particulate stream in one or more sweeps at variable rates of speed, either by pneumatic or electric drive. Further, the sample exhibits great flexibility in use; it can be used for high temperature applications, and at atmospheric, positive or negative pressure. The sampler is especially valuable for the sampling of exceedingly small size particles, including powders, flakes and granular materials, as well as photographic scrap material, paper scrap, and the like.

BRIEF DESCRIPTION OF THE DRAWINGS

FIG. 2 is a top view, taken along line 2—2 of FIG. 4;

FIG. 3 is a top view of the sampler shown in FIG. 1;

FIG. 4 is a side view of the sampler shown in FIG. 2;

FIG. 5 is an enlarged fragmentary view of the collecting head, with cap positioned thereon;

FIG. 6 is a side view of another embodiment of this invention;

FIG. 7 is a top view of the sampler shown in FIG. 6; and

FIG. 8 is a side view of the sampler shown in FIG. 6.

DESCRIPTION OF THE PREFERRED EMBODIMENTS

Figure 1:
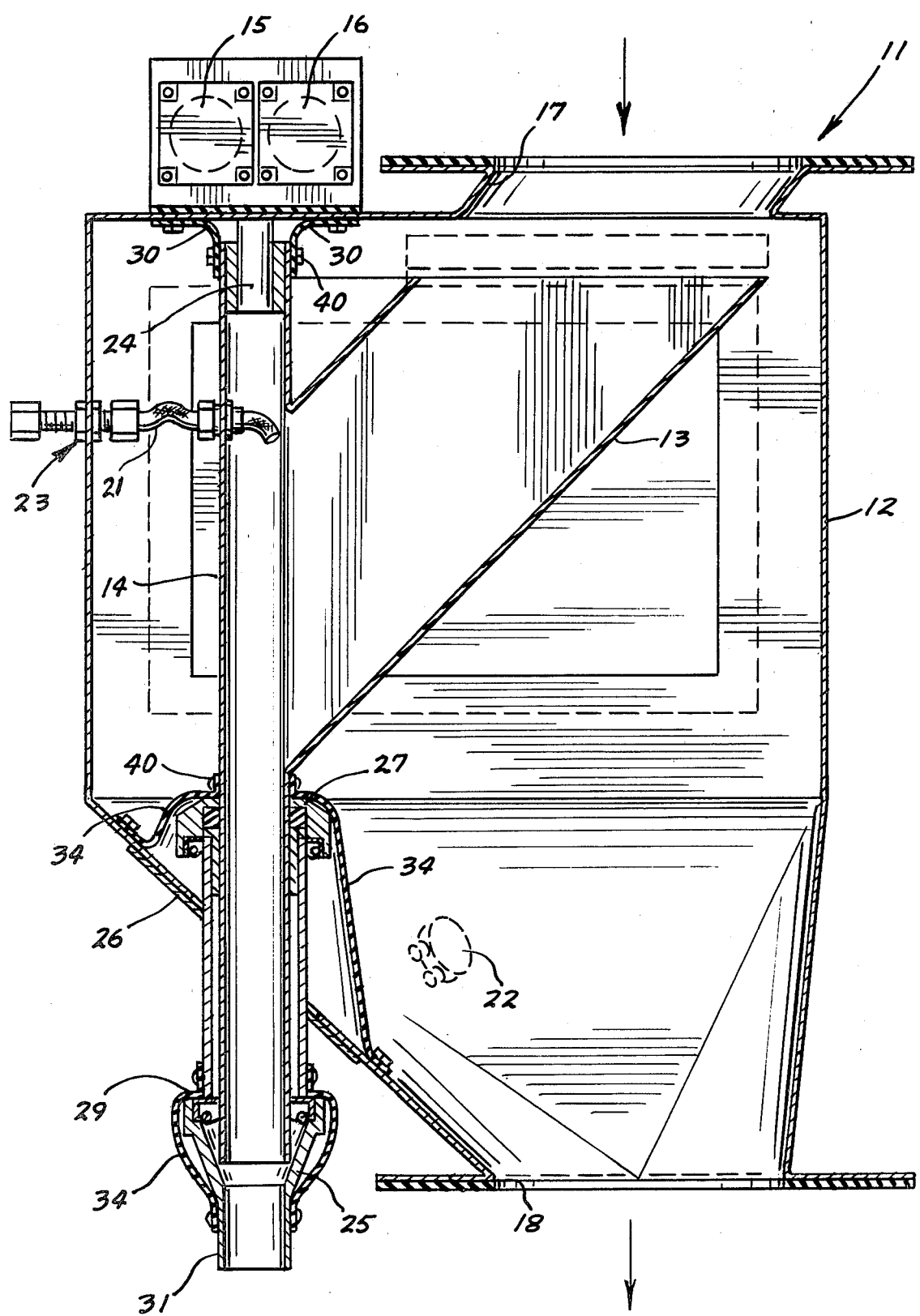
FIG. 1 is a cross sectional side view of the automatic sampler of this invention.

Referring to FIG. 1 of the drawings, sampler 11 comprises a sealed housing 12 containing therein collecting head 13 extending upwardly from sleeve 14 at a 45° angle from the horizontal, and rotary air cylinders 15, 16, mounted on the upper surface of housing 12. Sampler 11 can be used in obtaining samples of any free-flowing particulate matter in inclined or vertical spouts of gravity or pneumatic conveying systems. Housing 12 has entrance port 17 and exit port 18 for connection to the spout of such system, with the inner portion of housing 12 located between entrance port 17 and exit port 18, defining a central flow passage for the flow of particulate material through sampler 11 in the direction of the arrows. Vibrator 22 is disposed below collecting head 13 to insure continuous flow of particulate material through housing 12. Fitting 23 with hose 21 permits purging of air from the system.

Sleeve 14 is mounted within housing 12 on shaft 24, which shaft is in turn operably connected with air cylinders 15, 16. The lower portion of sleeve 14 is mounted on support guide 25 secured by plate 26 to the underside of housing 12, with bushings 27–29 contacting the outer surface of sleeve 14. Representative samples pass through the collecting head and interior of sleeve 14 and out the end of discharge tube 31, as will be discussed in more detail below.

Collecting head is triangularly shaped, with its hypotenuse running from the lower portion of housing 12 upwardly and away from its mounting on sleeve 14, the bottom of head 13 angling upward at an angle of about 45°. Sample particulate material passes along the bottom of head 13 under gravity, and into the interior of sleeve 14.

Neoprene seals 30 are secured to the underside of the upper wall of housing 12 and fitted around the upper end of sleeve 14, and neoprene seals 34 are secured to the bottom wall of housing 12 and fitted around the lower end of sleeve 14, to completely seal off the interior of housing 12. Rings 40 rotatably secure seals 30, 34 to sleeve 14. This sealing arrangement makes the sampler entirely dust free.

Referring to FIG. 2, collecting head 13 is shown in solid lines half way through its passage from one side of the central flow passage to the other, such side positions being indicated by dotted lines. Cap 32 having elongated slot 33 is secured across the open upper portion of collecting head 13, cap 32 being interchangable with other caps having wider or narrower widths, such that the opening of the collecting head can be adjusted according to the material being sampled.

Referring to FIG. 3, it it seen that entrance port 17 is slightly off center from the placement of the exit port 18, with collecting head 13 extending entirely across the central flow passage extending from entrance port 17 to exit port 18. Rotary air cylinders 15, 16, which can be four inch stroke oiless air cylinders having 2 and ½ inch bores, have piston rods and links (not shown) operably connected to shaft 24, as is known in the art. Operation of rotary air cylinders 15, 16 can be accomplished by using solenoids, to effect rotation of shaft 24, thereby causing swinging motion of collecting head 13 from one side of the central flow passage to the other. Collecting head 13 can be swung from one side to the other in one cycle of the sampler, or collecting head 13 can be moved back and forth one or more times to accomplish sampling.

Referring to FIG. 4, rotary air cylinders 15, 16 are mounted on the upper surface of housing 12 by means of bracket 37. Doors 38, having neoprene seals along their inside inner edges, are bolted to opposite side of housing 12, and have handles 39, to allow entrance into the interior of sampler 11 for inspection and/or replacement of collecting head 13, and to allow insertion of different size caps on the collecting head. Explosion proof limit switch 41 is secured to housing 12 by bracket 42, limit switch 41 being operably connected to doors 38 by means of connection 43.

A typical cap 32 for the upper portion of collecting head 13 is shown in FIG. 5. Upper portion 44 of collecting head 13 has opening 45, over which is inserted cap 32. Cap 32 has an elongated slot 33, as best seen in FIG. 3, the width of elongated slot 33 varying from the cap to the next, to allow for an adjustable opening in the collecting head. For example, when finer particulate matter is to be sampled, it may be desired to use a cap having a narrow width, whereas when coarser material is to be sampled, a greater slot width can be advantageously used.

A second embodiment of the invention is shown in FIG. 6, where collecting head 46 of sampler 50 is disposed on sleeve 47 rotatably disposed within sealed housing 48, with sealed housing 48 having aligned entrance ports 49, 51. Collecting head 46 is triangularly shaped with its hypotenuse extending at and angle of approximately 40° with the horizontal. The upper portion of collecting head 46 extends entirely across the central flow passage, defined by the area between entrance and exit ports 49, 51, with the upper portion of collecting head 46 having inserted thereon a cap 52. As with the caps used on collecting heads in the previously described embodiment, cap 52 has an elongated slot 56 confronting entrance port 49 and extending thereacross, with caps having slots of varying widths being insertable on collecting head 46. A single, hinged access door 53 is disposed adjacent the outer end of collecting head 46, for inspection of the interior of housing 48 and for replacement of collecting head 46 or adjustable caps 52.

Referring to FIG. 7, rotary air cylinder 54, mounted on the upper surface of housing 48 by means of bracket 55, operates to swing collecting head 46 through a 90° arc from one side of the central flow passage to the other, bringing the elongated slot 56 of cap 52 entirely across the stream of particulate matter passing through the sampler. Rotary air cylinder 54 can be any conventional air cylinder, such as one having a bore of approximately 2 inches and a displacement of about 4 inches.

Referring to FIG. 8, rotary air cylinder 54 is operably connected to sleeve 47 by shaft 57. Circular bushing 58 extends around shaft 57 and contacts the upper portion of sleeve 47. Neoprene seals 59 extend across the entire upper portion of housing 48 to make the interior of the sampler completely dust tight. Similarly, fitting 61 seals the mounting of the lower portion of sleeve 47 in housing 48, with discharge tube 62 extending therefrom.

The sampler of this invention is usable on inclined or vertical spouts. Location for the sampler should be as close to the entrance of the spout as possible. For installation, a section of spout the same length as the flange to flange length of the sampler is removed, and the flanges of the sampler are welded to the spout and the sampler is bolted in place. A control box, not shown in the drawings, can be disposed on the sampler for automatic sampling purposes, the control box being mounted in any convenient, vibration free location. A flexible hose is run from the discharge tube of the sampler to any desired collection point.

In operation, the rheostat on the control box is turned to a desired setting for determining the speed at which the collecting head moves across the product flow. Small rheostat settings represent slower speeds of the collecting head, and, consequently, larger sample sizes. As noted, the sample size may be changed by changing the cap covering the upper portion of the collecting head, by opening the housing door and substituting one cap for another. The control box may also have a timer which can be set to determine how often a sample is taken.

Upon movement of the collecting head across the product flow, particulate matter will pass through the elongated slot of the cap, down through the inner portion of the sleeve and out the discharge tube at the bottom of the sampler, for passage through flexible hosing to the collection point. The collecting head cuts across the entire material stream, thereby assuring a completely representative sample.

It is claimed:

1. Apparatus for drawing a representative sample of flowing particulate material from the spout of a conveying or dispensing system, comprising;
   an enclosed housing with entrance and exit ports for connection into a section of the spout, the housing having an open interior with an unobstructed central flow passage permitting free flow of particulate material therethrough,
   a sample collecting head mounted within the housing for swinging movement about an axis parallel to that of the central flow passage, such that the collecting head can be swung from one side of the central flow passage to the other, passing entirely through the central flow passage, with the head having an elongate opening confronting the entrance port, and
   means for swinging the collecting head across the central flow passage, and said means comprises at least one rotary air cylinder secured to the sealed housing for producing such swinging.

2. The apparatus of claim 1 wherein the collecting head is integrally formed with a hollow sleeve mounted for swinging movement about an axis parallel to that of the central flow passage, the upper portion of the hollow sleeve being secured to a rotatably oscillatable shaft extending through the upper portion of the housing and being operably connected to the rotary air cylinder secured thereto, rotary bearing means connecting the lower portion of the hollow sleeve to the underside of the housing.

3. The apparatus of claim 2 additionally comprising neoprene seals between the upper portion of the hollow sleeve, and the adjacent portions of the housing, and also between the lower portion of the hollow sleeve, and the underside of the housing such that the interior of the sealed housing is completely dust tight.

4. Apparatus for drawing a representative sample of flowing particulate material from the spout of a conveying or dispensing system, comprising;
   an enclosed housing with entrance and exit ports for connection into a section of the spout, the housing having an open interior with an unobstructed central flow passage permitting free flow of particulate material therethrough,
   a sample collecting head mounted within the housing for swinging movement about an axis parallel to that of the central flow passage, such that the collecting head can be swung from one side of the central flow passage to the other, passing entirely through the central flow passage, with the head having an elongate opening confronting the entrance port, the portion of the collecting head having the elongate opening is adapted to receive thereon replaceable caps having elongate openings corresponding to that of the collecting head, with the width of the elongate openings of the caps varying from cap to cap, and
   means for swinging the collecting head across the central flow passage.

5. Apparatus for drawing a representative sample of flowing particulate material from the spout of a conveying or dispensing system, comprising
   an enclosed housing having an upright flow passage therethrough and having a top entrance port and a bottom exit port for connection into a section of the spout,
   a sample collecting head mounted within the housing for swinging oscillatory movement about an upright axis parallel to the central flow passage, the sample collecting head having an elongate sample receiving slot-like opening oriented transversely of the central flow passage and confronting the top entrance port, the sample collecting head and the housing being cooperatively shaped to accommodate swinging by the sample collecting head to move the sample collecting opening of the head entirely across the flowing stream of material in the central flow passage, and
   collector head driving means on the housing and powered independently of the flow of particulate material through the flow passage, the driving means being connected with the collecting head to swing the collecting head transversely across the central flow passage in one direction and then swing the head across the flow passage in the other direction while maintaining the sample receiving opening of the head in a plane which is transverse to the flow of material through the central flow passage and thereby obtain a representative sample of flowing material from all portions of the stream of flowing material through said central flow passage.

6. The apparatus according to claim 5 and the driving means including an air cylinder swinging the head.

* * * * *